United States Patent
Therin et al.

(10) Patent No.: US 6,971,252 B2
(45) Date of Patent: Dec. 6, 2005

(54) PROSTHETIC KNIT WITH VARIABLE PROPERTIES

(75) Inventors: Michel Therin, Lyons (FR); Alfredo Meneghin, Anse (FR)

(73) Assignee: Sofradim Production, Trevoux (FR)

( * ) Notice: Subject to any disclaimer, the term of this patent is extended or adjusted under 35 U.S.C. 154(b) by 0 days.

(21) Appl. No.: 10/937,316

(22) Filed: Sep. 10, 2004

(65) Prior Publication Data

US 2005/0070829 A1    Mar. 31, 2005

(30) Foreign Application Priority Data

Sep. 16, 2003   (FR) .................................. 03 10853

(51) Int. Cl.$^7$ ............................................. D04B 21/20
(52) U.S. Cl. ........................................ 66/170; 66/195
(58) Field of Search ..................... 66/192, 195, 203, 66/204, 205, 207, 233, 169 R, 170; 623/1.5

(56) References Cited

U.S. PATENT DOCUMENTS

| | | | | |
|---|---|---|---|---|
| 4,193,137 A | * | 3/1980 | Heck .......................... | 66/195 |
| 5,732,572 A | * | 3/1998 | Litton ......................... | 66/195 |
| 6,408,656 B1 | * | 6/2002 | Ory et al. .................... | 66/195 |
| 6,540,773 B2 | * | 4/2003 | Dong .......................... | 66/195 |
| 6,554,855 B1 | * | 4/2003 | Dong .......................... | 66/195 |
| 2003/0100954 A1 | * | 5/2003 | Schuldt-Hempe et al. ............................................................ | 623/23.72 |

FOREIGN PATENT DOCUMENTS

| | | |
|---|---|---|
| FR | 2 779 937 A1 | 12/1999 |
| WO | WO 01/52750 A1 | 7/2001 |
| WO | WO 01/80773 A1 | 11/2001 |
| WO | WO 02/28312 A1 | 4/2002 |
| WO | WO 2004/004600 A1 | 1/2004 |

* cited by examiner

*Primary Examiner*—Danny Worrell
(74) *Attorney, Agent, or Firm*—Oliff & Berridge, PLC

(57) ABSTRACT

An openwork prosthetic knit made in one piece, based on an arrangement formed by several sheets of yarns of a biocompatible polymer material, including a central band and two lateral bands on either side, respectively, of the central band, the elasticity of the knit in the central band being greater than the elasticity of the knit in each of the lateral bands at least two base sheets, a front sheet and a rear sheet, extending at least across the whole surface of the central band, the two base sheets being meshing sheets and defining a first weave, and at least two supplementary sheets, behind the rear base sheet, extending only across the respective surfaces of the lateral bands, the two supplementary sheets being sheets of partial weft and defining a second weave.

30 Claims, 4 Drawing Sheets

PROSTHETIC KNIT WITH VARIABLE PROPERTIES

Figure 1:
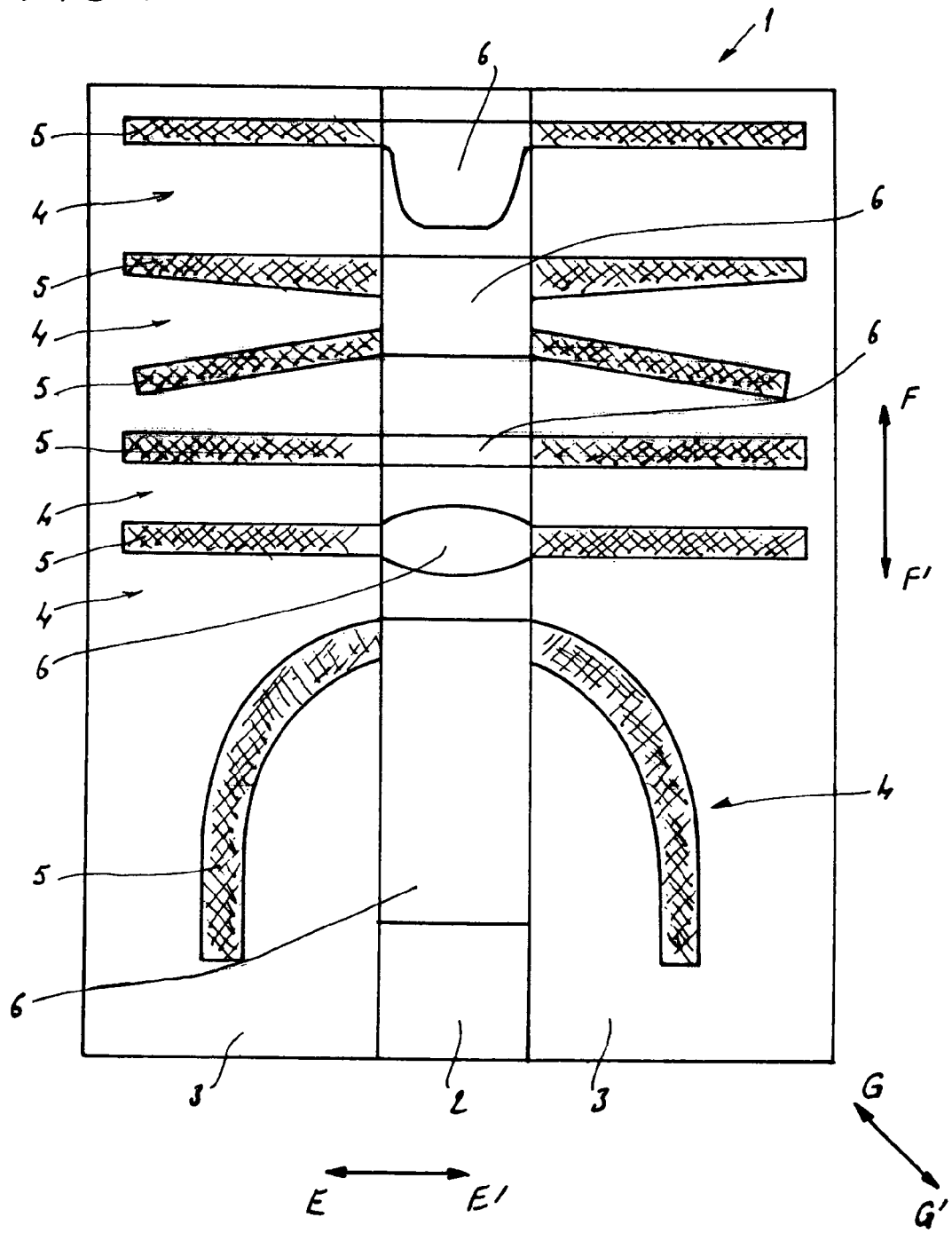

The present invention concerns a prosthetic knit with variable properties, in particular with variable mechanical strength and density, in at least one dimension or direction of extension of said knit, usable in particular in the form of bands or tapes cut out from said knit in the treatment of pelvic floor disorders, also called prolapses, especially in women. This reinforcement can also be used for preparing tapes for urethral support in the treatment of female stress urinary incontinence.

Surgical treatment of prolapses involves the use of reinforcements in the form of implants for supporting the prolapsed organ. The central part of the implant is arranged in the area of this organ and may be in contact with the latter so as to support it, while the lateral parts of the implant are fixed to stable anatomical elements such as the abdominal wall, the obturator membrane, the promontory of the sacrum, the sacrosciatic ligaments or the os pubis, for example by means of staples or sutures, or by simple tissue anchoring.

In a known manner, such a support implant has to meet a number of demands, and in particular it must have suitable mechanical strength in all directions, be biocompatible and flexible, and yet have a certain elasticity. These support implants must preferably be porous and non-aggressive in their central part supporting the organ. These support implants have to be able to be sutured. Finally, it is desirable that these support implants are adapted to the morphology of the patient.

Textile means for conforming, on the one hand, to the anatomy of the suburethral region and, on the other hand, to the surgical technique employed are known.

The documents WO 01/52750 and WO 02/28312 describe a suburethral support tape comprising an openwork knit, this knit being composed of two sheets of yarns across the whole surface of the tape. The knit formed is uniform, and the tape thus has the same properties of porosity, density, elasticity and mechanical strength across its whole surface, that is to say both in its central part and at its ends.

The surgical techniques for treating prolapses and stress urinary incontinence increasingly make use of reinforcements which have a central zone, placed under the organ to be supported, wider than the lateral ends intended to be anchored at a distance in the muscle and aponeurosis. The mechanical and biological properties expected of these separate parts are different.

At their ends, these support implants have to be able to be cut into narrow tapes of the order of 1 cm without unravelling or curling. By "curling" we mean, in the context of the present application, the spontaneous rolling-up of the tape about its longitudinal axis under tension along its length. These implants have to retain sufficient mechanical properties in this form, particularly of strength, while at the same time limiting as far as possible the release of particles, that is to say yarn ends, when they are stressed, and they must allow mechanically stable tissue anchoring.

By contrast, in the central part of the implant, which is the part supporting the urethra or prolapsed organ, it is particularly important that the implant has a minimal density, maximum porosity and great pliability and great elasticity, the tear strength and resistance to curling in this part, not intended to be cut into fine tapes, being less important than at the ends. The reason is that, since this central part may possibly be in contact with the organ to be supported, it must preferably be minimally aggressive relative to the wall of the hollow viscera such as the bladder, vagina, rectum or urethra, so as to minimize the risks of erosion.

These implants, and in particular the tapes which can be cut out from them, must also preferably be non-unravelling.

Finally, as patients have different morphologies, it is important that the surgeon is able to fashion the implant at the operating site, at the time of the intervention, so as to be able to adapt its configuration or shape to that of the patient's body.

Thus, it would be advantageous to have a knit which can be cut as desired, having a zone of particularly low density, with wide pores, and flexible and elastic, which could correspond to the central part of the implant, and particularly resistant zones which could correspond to the lateral ends of the implant, and being able to be cut in widths of for example less than 1 cm wide, while resisting curling and unravelling.

The document WO 01/80773 describes an openwork prosthetic knit whose central part has an elasticity greater than that of the peripheral parts, the central part being intended to be deformed in order to form a protuberance. However, this knit is formed using an arrangement of several sheets of yarns, of which only one is meshing, the latter being a chain weave. By "meshing sheet" we mean, in the context of the present application, a sheet of yarns for which the chart followed for knitting the yarns leads to the formation of meshes. Given that it comprises only one meshing sheet in a chain weave, the knit described in WO 01/80773 is imbalanced and, in its peripheral parts, does not permit cutting-out of non-unravelling parts of small width, for example equal to 1 cm wide, and resistant to tearing and to curling.

The present invention aims to overcome this problem by generally proposing a knit of variable density in at least one direction or dimension of said knit, ready to be cut, usable in particular for easily and quickly producing or obtaining support implants for the treatment of prolapses and stress urinary incontinence, comprising a central band, in the direction of production of the knit, with low density, wide porosity, elasticity and pliability, and two lateral bands, on either side of the central band, each having a greater density so as to afford high resistance to tearing and to curling, this knit being made in one piece and having no excess thickness or lack of continuity from one band to the other, and furthermore permitting cutting of tapes with ends of small width, for example from 1 cm to 3 cm.

The present invention concerns an openwork prosthetic knit made in one piece, based on an arrangement formed by several sheets of yarns of a biocompatible polymer material, comprising, in a continuous manner in the direction of production of the knit, a central band and two lateral bands on either side, respectively, of the central band, the elasticity of the knit in the central band being greater than the elasticity of the knit in each of the lateral bands, characterized in that it comprises i) at least two base sheets, a front sheet and a rear sheet, extending at least across the whole surface of the central band, said two base sheets being meshing sheets and defining a first weave, and ii) at least two supplementary sheets, behind said rear base sheet, extending only across the respective surfaces of the lateral bands, said two supplementary sheets being non-meshing sheets of partial weft and defining a second weave.

The present invention also concerns a method for producing an openwork prosthetic knit made in one piece, based on an arrangement formed by several sheets of yarns of a biocompatible polymer material, comprising, in a continuous manner in the direction of production of the knit, a central band and two lateral bands on either side, respectively, of the central band, the elasticity of the knit in the central band being greater than the elasticity of the knit in each of the lateral bands, characterized in that it comprises the following step:

production of a knit on a warp-knitting machine or Rachel loom, with two base sheets, a front base sheet and a rear base sheet defining a first weave, and two supplementary sheets defining a second weave, the two base sheets being threaded continuously or intermittently at least across the width of the central band, each of the base sheets being obtained from one guide bar, the chart followed for knitting the yarns of each base sheet leading to the formation of meshes, the two supplementary sheets being threaded intermittently only across the respective widths of the lateral bands, each of the supplementary sheets being obtained from one guide bar, the chart followed for knitting the yarns of each supplementary sheet leading to a non-meshing partial weft.

The knit according to the invention makes it possible to easily cut out support implants having a central part of particularly low density which is porous, flexible and elastic, and ends which are particularly resistant to tearing and curling, even if these ends have a width of from 1 cm to 3 cm, for example.

By virtue of the presence of at least two meshing sheets on the central band of the knit, the latter is particularly stable.

In a preferred embodiment of the invention, the two base sheets extend across the whole of the surface of the knit, that is to say across the surface of the central band and across the respective surfaces of the lateral bands. In this case, by virtue of the presence of at least two meshing sheets across the whole knit, the latter is particularly balanced and stabilized dimensionally across its whole surface, that is to say it does not risk losing its minimum qualities of elasticity and strength in any direction or dimension, whether longitudinal, transverse or diagonal, and for whatever band, either central or lateral, after cutting.

Moreover, by virtue of the specific knitting of the knit involving addition, on two base sheets, of two partial weft sheets on the lateral parts, the knit according to the invention is formed in one piece and has no excess thickness or discontinuity of appearance from one band to the other.

In the present application, the term "prosthetic knit" means a knit intended to be implanted in the human or animal body in the form of a prosthesis or of any other part formed at least partially with said knit.

In the present application, "openwork knit" means a knit whose weave or weaves determine cells or gaps in the thickness of the knit, these cells or gaps being able to form channels opening out on either side of the knit. Such an openwork knit permits better tissue integration. In particular, by virtue of its specific knitting, the prosthetic knit according to the invention has an openwork structure across the whole of its central and lateral bands. In particular, the porosity of the knit in the central band is greater than the porosity of the knit in each of the lateral bands.

In the present application
   the mass per unit area of a knit is measured according to ISO 3801,
   the breaking strength of a knit in the longitudinal direction and in the transverse direction is measured according to ISO 13934-1.

In a preferred embodiment of the invention, the mass per unit area, or the density, of the knit in each of the lateral bands is greater than the mass per unit area, or density, of the knit in the central band. In a preferred embodiment of the invention, the mass per unit area of the knit in each of the lateral bands is at least twice as great as the mass per unit area of the knit in the central band.

In a preferred embodiment of the invention, the breaking strength of the knit in the longitudinal direction and in the transverse direction in the area of each lateral band is at least twice as great as the breaking strength of the knit in the longitudinal direction and in the transverse direction in the area of the central band.

Thus, the knit according to the invention has an elasticity in its central band greater than the elasticity in each of the lateral bands.

In one embodiment of the invention, the central band has a mass per unit area ranging from 15 to 50 $g/m^2$, and preferably ranging from 25 to 35 $g/m^2$. Preferably, the breaking strength of the knit in the central band is about 90 N in the longitudinal direction and in the transverse direction.

In one embodiment of the invention, each lateral band has a mass per unit area ranging from 60 to 80 $g/m^2$, and preferably of the order of 70 $g/m^2$. Preferably, the breaking strength of the knit in each lateral band is about 200 N in the longitudinal direction and in the transverse direction.

The knit according to the invention is preferably formed from yarns, monofilaments or multifilaments, of a biocompatible polymer material chosen from among polypropylene, polyester, polyamide and mixtures thereof.

Preferably, the monofilament yarns have a diameter ranging preferably from 0.06 mm to 0.18 mm. The multifilament yarns preferably have a linear density ranging from 44 dtex to 100 dtex.

The first weave of the knit according to the invention is defined by a front base sheet and a rear base sheet, each of these sheets being obtained, for example, from a guide bar of a warp-knitting machine or Rachel loom, the chart followed for knitting the yarns of each sheet leading to the formation of meshes. In a preferred embodiment of the invention, this chart leads to the formation of an open-mesh atlas pattern. By "atlas" pattern, we mean, in the context of the present application, a pattern obtained by the fact that each guide throws its yarn under one or more needles, several times in the same direction, then in the opposite direction. More preferably, this chart leads to the formation of an irregular open-mesh atlas pattern. By "irregular atlas" we mean, in the context of the present application, an atlas pattern whose consecutive meshes are formed on irregularly spaced columns.

In a preferred embodiment of the invention, the yarns of the front base sheet are knitted according to a chart 0-1/1-2/3-4/5-4/4-3/2-1// and the yarns of the rear base sheet are knitted according to a chart 5-4/4-3/2-1/0-1/1-2/3-4//. Preferably, the two guide bars of the base sheets are threaded continuously, that is to say across the whole width of the knit in the transverse dimension, one full, one empty, in other words one full guide, one empty guide, and they move symmetrically with respect to one another.

The second weave of the knit according to the invention is defined by two supplementary sheets, behind the rear base sheet, each of these two supplementary sheets being obtained, for example, from one guide bar of a warp-knitting machine or Rachel loom, the chart followed for knitting the yarns of each supplementary sheet leading to a non-meshing partial weft, and, consequently, not leading to the formation of meshes.

In a preferred embodiment of the invention, the first weave extends across the whole surface of the knit, and the two guide bars of the supplementary sheets move in partial weft with throws "underneath" in relation to the first weave. More preferably, the two guide bars of the supplementary sheets move in partial weft with throws "underneath" two and five needles. By virtue of this weft movement, it is possible to improve the transverse resistance of the knit in the area of the lateral bands while maintaining a low mass per unit area.

In a preferred embodiment of the invention, the yarns of one of the two supplementary sheets are knitted according to the chart 3-3/5-5/0-0/2-2/0-0/5-5//, and the yarns of the other supplementary sheet are knitted according to the chart 2-2/0-0/5-5/3-3/5-5/0-0//.

Preferably, the two guide bars of the supplementary sheets are threaded intermittently, that is to say only across the respective widths of the lateral bands, in the transverse dimension of the knit. Inside each lateral band, the two guide bars of the supplementary sheets are preferably threaded one full, one empty.

By virtue of the addition of two supplementary sheets obtained from partial weft bars on the lateral parts of the knit, the thickness of the knit is substantially equal across the whole surface of the prosthetic knit. This thickness will preferably be from 0.3 mm to 0.5 mm.

The prosthetic knit can additionally comprise other sheets of yarns in addition to the two base sheets and to the two supplementary sheets already described above. In this case, additional guide bars are added to the knitting machine in order to obtain as many additional sheets of yarns. For example, the prosthetic knit according to the invention can comprise two base sheets and three supplementary sheets, or else four supplementary sheets.

Another subject of the invention is the use of a prosthetic knit, such as has been defined above, for obtaining a prosthetic product for surgical use, in particular for obtaining a support implant for treating prolapses and stress urinary incontinence.

Another subject of the invention is a support implant for treating prolapses and stress urinary incontinence, obtained by cutting a prosthetic knit such as has been defined above.

By virtue of the particular properties of, on the one hand, the central band of the knit, namely low mass per unit area, high porosity, elasticity and pliability, and, on the other hand, of its lateral bands, namely breaking strength and resistance to curling, it is possible, in particular for the surgeon, to cut out directly from this knit a support implant which can be used for treating prolapses and stress urinary incontinence and which has, in its central part, low density, porosity, elasticity and pliability, and, in the area of its ends, resistance to tearing, these ends not curling up, even when cut into fine strips, for example of the order of 1 cm wide.

Figure 2:
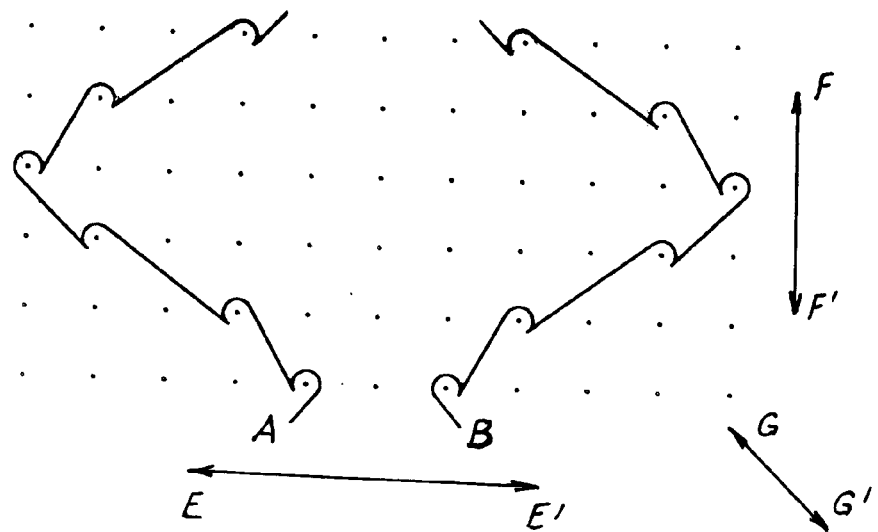
Figure 3:
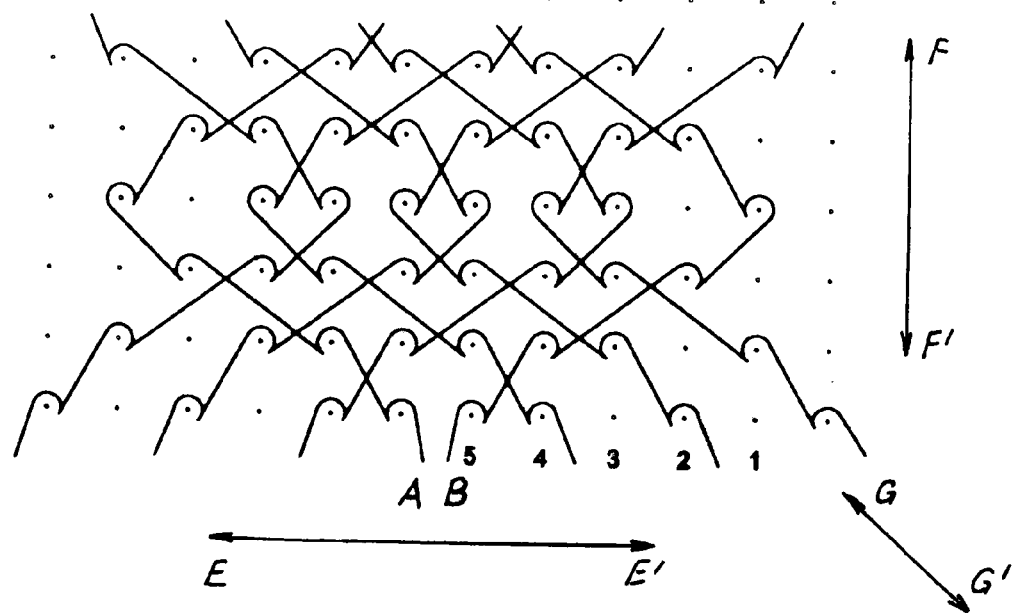
Figure 4:
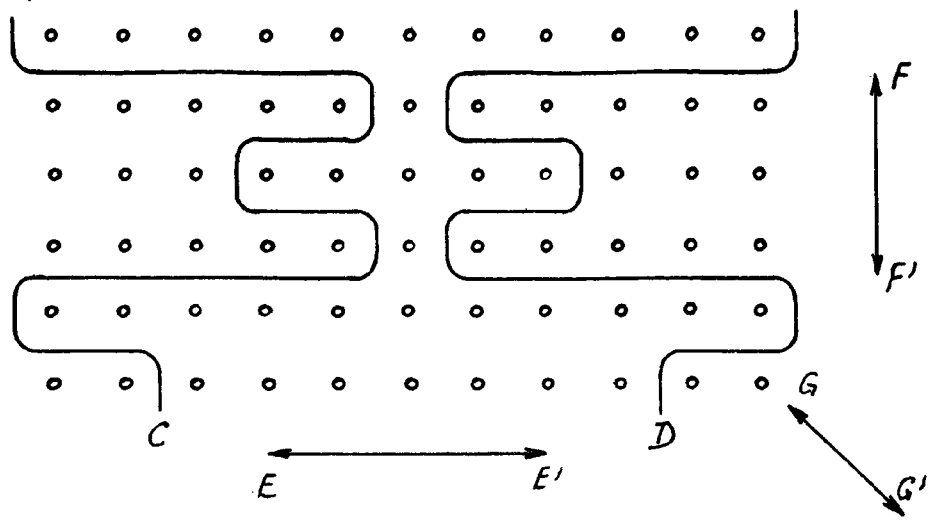
Figure 5:
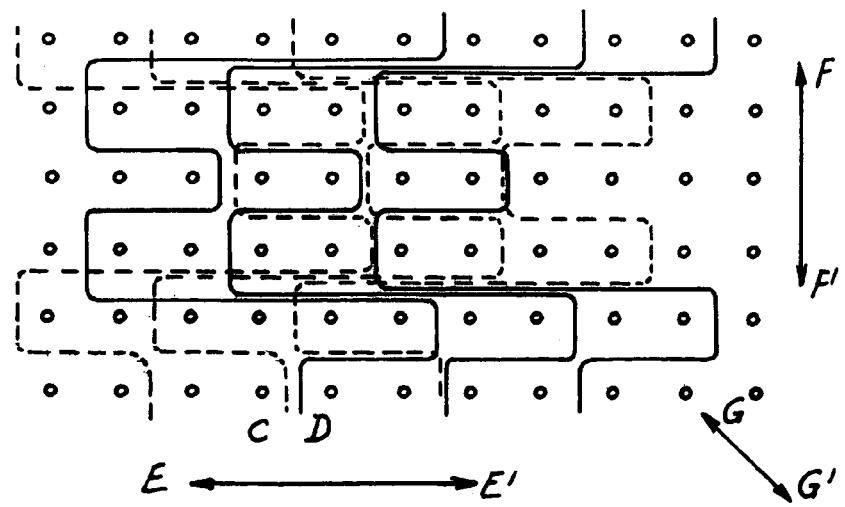
Figure 6:
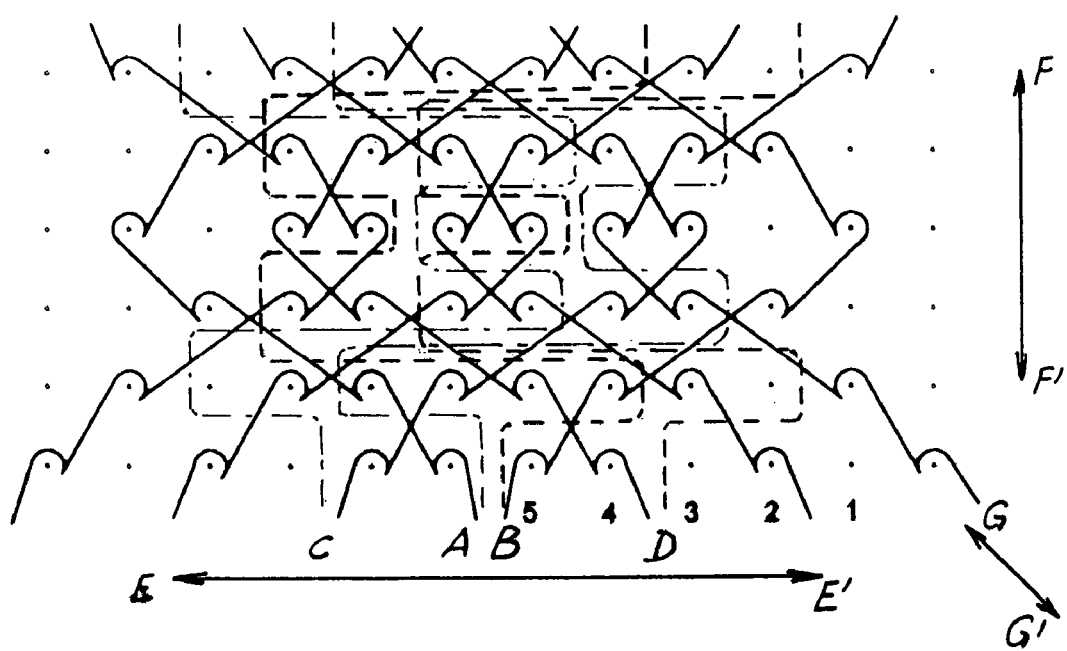

The invention will be better understood from the following description in which reference is made to the attached drawing, where:

FIG. 1 shows a prosthetic knit according to the invention, comprising preliminary cutouts for the formation of support implants of different shapes for treating prolapses and stress urinary incontinence, FIG. 2 shows a simplified diagrammatic drawing of a yarn of the front base sheet (A) and a yarn of the rear base sheet (B) of a first weave of a knit according to the invention, FIG. 3 shows a simplified diagrammatic drawing of the first weave according to FIG. 2, FIG. 4 shows a simplified diagrammatic drawing of a yarn (C) of a first supplementary sheet and a yarn (D) of a second supplementary sheet, of a second weave of a knit according to the invention, FIG. 5 shows a simplified diagrammatic drawing of the second weave according to FIG. 4, FIG. 6 shows a simplified diagrammatic drawing of the combination of the first weave and of the second weave according to FIGS. 2 and 4, respectively.

For each FIG. 1 to 6, E–E' defines the transverse direction or dimension of the knit, F–F' the longitudinal direction or dimension of the knit, and G–G' the diagonal direction or dimension of the knit.

Referring to FIG. 1, a prosthetic knit 1 according to the invention is shown, comprising a central band 2 with two base sheets, and two lateral bands 3 with four sheets, namely the two base sheets and two supplementary sheets. This knit 1 comprises cutouts defining support implants 4 for treating prolapses and stress urinary incontinence, whose central parts 6 are cut out in the area of the central band 2 of the knit 1, and whose ends 5 are cut out in the area of the two lateral bands 3, respectively, of the knit 1. Thus, it is possible to cut out implants 4 having a symmetrical or asymmetrical bulged central part 6. It is possible to cut out implants 4 whose ends 5 are perpendicular, or by contrast oblique, with respect to the central part 6. It is also possible to cut out implants 4 which have, for example, two ends 5 on each side of the central part 6. By virtue of the construction of the prosthetic knit explained hereinbelow, these implants 4 have great pliability, high porosity and great elasticity in their central part 6 intended to be in contact with the organ to be supported, whereas they have a good resistance to tearing and to curling in the area of their ends 5 intended to be anchored to the abdominal wall for example, even when these ends have a width of from 1 cm to 3 cm, for example.

The prosthetic knit may also not present a particular cutout. In this case, the surgeon can cut out the particular shape he wants, so as to fashion a support implant for treating prolapses and stress urinary incontinence, the simplicity of use of the prosthetic knit according to the invention making it possible, inter alia, to produce implants and tapes of all shapes, even very complex ones.

Referring to FIGS. 2 and 3, these show the front (A) and rear (B) yarns forming, respectively, the front base sheet and the rear base sheet, producing the base knit of a prosthetic knit according to the invention, that is to say a first weave of a knit according to the invention. This first weave can extend across the whole surface of the knit or only across the surface of the central band 2 of the knit.

FIG. 2 shows just one front yarn (A) and one rear yarn (B) in order to show clearly the movements of the yarns. Referring to FIGS. 2 and 3, the knit shown is formed on a warp-knitting machine or Rachel loom with two guide bars threaded one full, one empty, moving symmetrically with respect to one another. Referring to FIG. 3, several front yarns and several rear yarns are shown, and the pattern formed is an open-mesh atlas with progressions under two and three needles. For this weave, the values of longitudinal, transverse and diagonal elasticity are similar.

The knitting chart shown diagrammatically in FIGS. 2 and 3 is the following chart:
  for the front sheet: 0-1/1-2/3-4/5-4/4-3/2-1//,
  for the rear sheet: 5-4/4-3/2-1/0-1/1-2/3-4//.

Referring to FIG. 4, this shows a yarn (C) of a first supplementary sheet and a yarn (D) of a second supplementary sheet forming a second weave of a prosthetic knit according to the invention. This second weave extends only across the lateral bands 3 of the knit. Referring to FIG. 5, several yarns (C, D) of these two supplementary sheets are shown: for better understanding, the yarns C are shown in dashed lines and the yarns D are shown in solid lines. To the person skilled in the art, it will be clear from this figure that the pattern produced does not form meshes. By virtue of the presence of numerous horizontal returns of yarns C and D, the breaking strength in the transverse direction of this second weave is particularly high.

The knitting chart shown diagrammatically in FIGS. 4 and 5 is the following chart:
for the first supplementary sheet, according to yarn C, 3-3/5-5/0-0/2-2/0-0/5-5//,
for the second supplementary sheet, according to yarn D, 2-2/0-0/5-5/3-3/5-5/0-0//.

Referring to FIG. 6, this shows the combination of the first weave according to FIGS. 2 and 3 and of the second weave according to FIGS. 4 and 5 in the case where the first weave extends across the whole surface of the knit. For better understanding, the yarns A and B are shown in solid lines, the yarns C are shown in dot-and-dash lines, and the yarns D are shown in dashed lines. This combination takes place only starting from the junction between the central band and a lateral band of the prosthetic knit, and as far as the corresponding border of the latter. For this purpose, the two supplementary sheets defining the second weave are formed on the same loom as is used for the first weave, by addition of two guide bars threaded intermittently, that is to say only across the width of the lateral bands. These two supplementary guide bars also move symmetrically with respect to one another.

Referring to this FIG. 6, the central band 2 of the knit is produced with two guide bars, while the lateral bands 3 of the knit are produced with four guide bars. Moreover, it will be seen from FIGS. 3 and 5 that all the yarns of the knit move under five needles in total, making it possible to obtain a better hold of the yarns, with less risk of fraying of the edges and of unravelling. Finally, it will be seen from FIG. 6 that the holes or cells defined by the first weave are not blocked by addition of the second weave, and the knit obtained thus has an openwork structure across the whole of the central and lateral bands.

Thus, in the area of the lateral bands 3 of the knit, the yarns C and D of the two supplementary sheets do not form meshes, but partial wefts, and they are received inside the meshes formed by the first weave. This specific arrangement of the base sheets and of the supplementary sheets makes it possible to add yarns, and thus material, to the lateral bands 3 of the knit without creating an excess thickness or a visible break between the central band 2 and the lateral bands 3. Moreover, by virtue of this addition of material, the particular nature of the second weave and the specific arrangement of the sheets relative to each other, the knit has, at each of its lateral bands 3, a breaking strength and resistance to curling greater than that at its central band.

In the case where the first weave extends only across the central band 2 of the prosthetic knit, the central band 2 is produced with two guide bars threaded intermittently only across the width of the central band 2, and the lateral bands 3 are produced with two other guide bars also threaded intermittently, but this time only across the respective widths of the lateral bands 3.

On leaving the loom, the knit obtained is preferably subjected to a thermosetting operation which further improves its stabilization in the longitudinal and transverse directions.

The knit according to the invention thus permits cutting-out of fine tapes in the area of the lateral bands of the knit, for example tapes of at least 1 cm, without risk of these curling or tearing under the effect of a traction along the length of said tapes.

EXAMPLE

A knit according to the invention was produced from a monofilament yarn of polypropylene, diameter 0.10 mm, on a Rachel loom, with the following charts for the various sheets:
front base sheet: 0-1/1-2/3-4/5-4/4-3/2-1//,
rear base sheet: 5-4/4-3/2-1/0-1/1-2/3-4//,
1st supplementary sheet: 3-3/5-5/0-0/2-2/0-0/5-5//,
2nd supplementary sheet: 2-2/0-0/5-5/3-3/5-5/0-0//.

The guide bars of the front and rear base sheets were threaded continuously, one full, one empty. The gauge used was of 24 needles, one full, one empty, i.e. 12 needles per inch.

The guide bars of the two supplementary sheets were threaded intermittently across the respective widths of the lateral bands. Inside each lateral band, the guide bars were threaded one full, one empty. The gauge used was of 24 needles, one full, one empty, i.e. 12 needles per inch.

On leaving the loom, the knit was subjected to a thermosetting operation.

The width of the central band 2 was 5 cm. The width of each lateral band 3 was 20 cm. A tape measuring 10 mm in width and 150 mm in length was cut out from a lateral band of the knit. We then measured the breaking strength of this tape in the longitudinal direction of the knit, that is to say along the width of the tape, in the transverse direction of the knit, that is to say along the length of the tape, and in the diagonal direction of the tape. The results were as follows:
breaking strength in the longitudinal direction, measured according to ISO 13934-1, for which the width of the specimen was 10 mm and the length of the specimen was 150 mm: 31 N,
breaking strength in the transverse direction, measured according to ISO 13934-1, for which the width of the specimen was 10 mm and the length of the specimen was 150 mm: 42 N,
breaking strength in the diagonal direction, measured according to ISO 13934-1, for which the width of the specimen was 10 mm and the length of the specimen was 150 mm: 33 N.

The tape with width 10 mm thus cut out from a lateral part of the knit according to the invention has excellent tensile strength and is thus eminently suitable for production of a support implant for treating prolapses and stress urinary incontinence.

The present invention is not limited to the embodiments described by way of examples in the present application. For example, the width of the central band and that of the lateral bands can vary.

In another embodiment of the invention, the central band 2 of the prosthetic knit is covered on at least one of its faces with a bioabsorbable material, for example collagen, the implant thus being particularly non-aggressive towards the organ that is to be supported.

What is claimed is:
1. Openwork prosthetic knit made in one piece, based on an arrangement formed by several sheets of yarns of a biocompatible polymer material, the knit comprising:
a central band in a continuous manner in the direction of production of the knit;

two lateral bands on either side, respectively, of the central band, an elasticity of the knit in the central band being greater than the elasticity of the knit in each of the lateral bands;

a front base sheet and a rear base sheet defining at least two base sheets, extending at least across the whole surface of the central band, said two base sheets being meshing sheets and defining a first weave; and at least two supplementary sheets, behind said rear base sheet, extending only across the respective surfaces of the lateral bands, said two supplementary sheets being non-meshing sheets of partial weft and defining a second weave.

2. The knit according to claim 1, wherein the two base sheets extend across the whole surface of the knit, in which the two base sheets extend across the surface of the central band and across the respective surfaces of the lateral bands.

3. The knit according to claim 1, wherein a mass per unit area of the knit in each of the lateral bands is at least twice as great as the mass per unit area of the knit in the central band.

4. The knit according to claim 1, wherein a breaking strength of the knit in a longitudinal direction and in a transverse direction in an area of each lateral band is at least twice as great as the breaking strength of the knit in the longitudinal direction and in the transverse direction in the area of the central band.

5. The knit according to claim 1, wherein the central band has a mass per unit area ranging from 15 to 50 g/m$^2$.

6. The knit according to claim 1, wherein a breaking strength of the knit in the central band is about 90 N in the longitudinal direction and in a transverse direction.

7. The knit according to claim 1, wherein each lateral band has a mass per unit area ranging from 60 to 80 g/m$^2$.

8. The knit according to claim 1, wherein a breaking strength of the knit in each lateral band is about 200 N in a longitudinal direction and in a transverse direction.

9. The knit according to claim 1, wherein the knit is formed from yarns, monofilaments or multifilaments, of a biocompatible polymer material chosen from among polypropylene, polyester, polyamide and mixtures thereof.

10. The knit according to claim 1, wherein the knit further comprises other sheets of yarns in addition to the two base sheets and to the two supplementary sheets.

11. The knit according to claim 1, wherein at least one face of the central band is covered, with a bioabsorbable material.

12. A method of use of the knit according to claim 1, wherein the method includes cutting the knit to a particular shape to form a support implant for treating prolapses and stress urinary incontinence.

13. The knit according to claim 1, wherein a support implant for treating prolapses and stress urinary incontinuence is obtained by cutting the knit.

14. The knit according to claim 13, wherein the support implant has a symmetrical or asymmetrical bulged central part.

15. The knit according to claim 13, wherein the support implant ends are perpendicular with respect to the central part.

16. The knit according to claim 13, wherein the support implant ends are oblique with respect to the central part.

17. The knit according to claim 13, wherein the support implant has two ends on each side of a central part.

18. A method of producing an openwork prosthetic knit made in one piece, based on an arrangement formed by several sheets of yarns of a biocompatible polymer material, the knit comprising:

producing a central band in a continuous manner in the direction of production of the knit;

producing two lateral bands on either side, respectively, of the central band, an elasticity of the knit in the central band being greater than the elasticity of the knit in each of the lateral bands; and utilizing a warp-knitting machine or Rachel loom, to produce a front base sheet and a rear base sheet that form two base sheets defining a first weave, the two base sheets being threaded continuously or intermittently at least across a width of the central band, each of the base sheets being obtained from one guide bar, wherein following a chart for knitting the yarns of each base sheet leads to the formation of meshes, and to produce the two supplementary sheets being threaded intermittently only across the respective widths of the lateral bands, each of the supplementary sheets being obtained from one guide bar, wherein following a chart for knitting the yarns of each supplementary sheet leads to a non-meshing partial weft.

19. The method according to claim 18, wherein the chart followed for knitting the yarns of each base sheet leads to the formation of an atlas pattern with open meshes.

20. The method according to claim 19, wherein the chart leads to the formation of an irregular open-mesh atlas pattern.

21. The method according to claim 20, wherein the yarns of the front base sheet are knitted according to the chart 0-1/1-2/3-4/5-4/4-3/2-1// and the yarns of the rear base sheet are knitted according the chart 5-4/4-3/2-1/0-1/1-2/3-4//.

22. The method according to claim 18, wherein two guide bars of the base sheets are threaded continuously, one full, one empty, and move symmetrically with respect to one another.

23. The method according to claim 22, wherein two guide bars of the supplementary sheets move in partial weft, with throws underneath in relation to the first weave.

24. The method according to claim 23, wherein two guide bars of the supplementary sheets move in partial weft with throws underneath two and five needles.

25. The method according to claim 24, wherein the yarns of one of the two supplementary sheets are knitted according to the chart 3-3/5-5/0-0/2-2/0-0/5-5//, and the yarns of the other supplementary sheet are knitted according to the chart 2-2/0-0/5-5/3-3/5-5/0-0//.

26. The method according to claim 23, wherein inside each lateral band, the two guide bars of the supplementary sheets are threaded one full, one empty.

27. The method according to claim 18, wherein additional guide bars are added to the loom in order to obtain as many additional sheets of yarns.

28. The method according to claim 18, wherein on leaving the loom, the knit is subjected to a thermosetting operation.

29. The knit according to claim 1, wherein the central band has a mass per unit area ranging from 25 to 35 g/m$^2$.

30. The knit according to claim 1, wherein each lateral band has a mass per unit area of about 70 g/m$^2$.

* * * * *